March 20, 1956 E. J. WEBBER Plant Pat. 1,464
ROSE PLANT
Filed Nov. 17, 1954
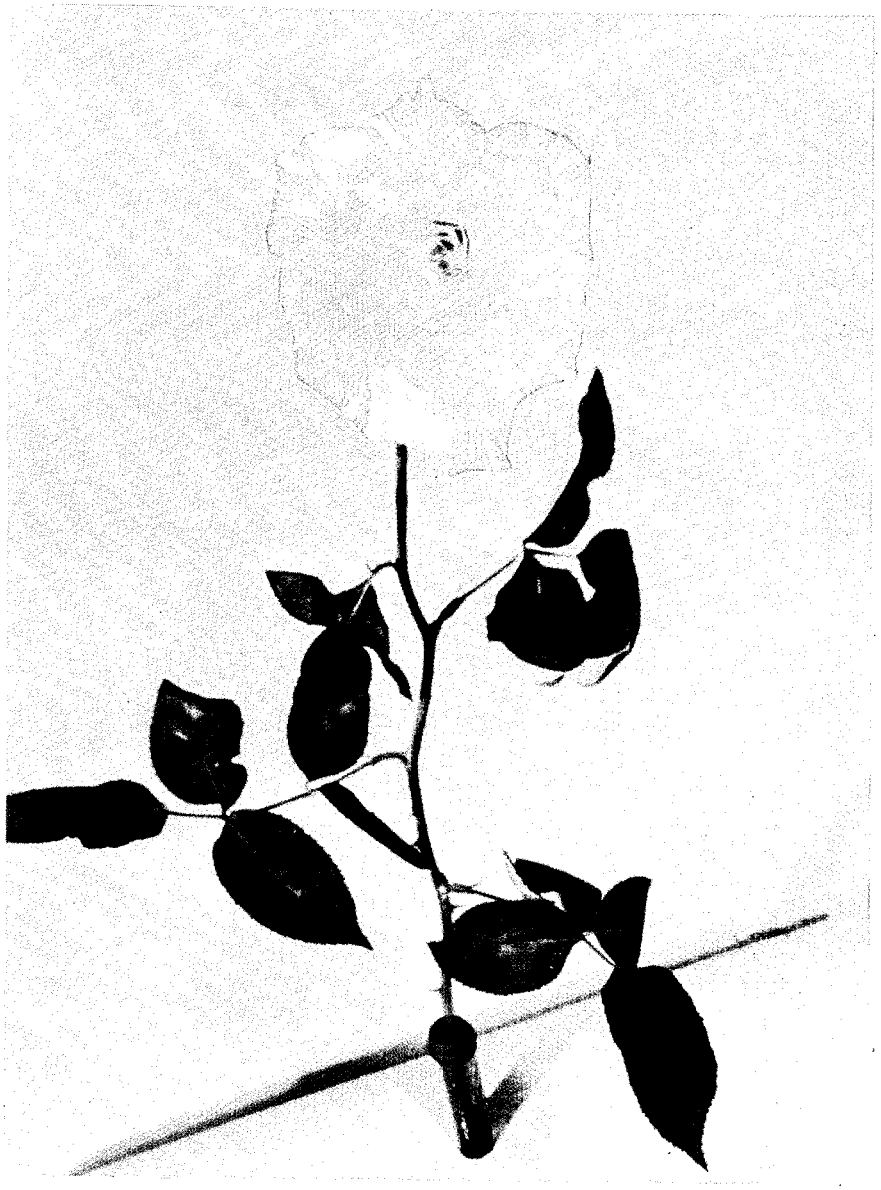
Edward J. Webber
INVENTOR.
BY Clarence A. O'Brien and Harvey B. Jacobson
Attorneys United States Patent Office Plant Pat. 1,464
Patented Mar. 20, 1956

1,464

ROSE PLANT

Edward J. Webber, Missoula, Mont.

Application November 17, 1954, Serial No. 469,563

1 Claim. (Cl. 47—61)

The new variety of tea rose plant herein described and illustrated is a sport of the rose plant "Briarcliff," unpatented.

Asexual reproduction of this new variety by cuttings at the greenhouse in Missoula, Montana, over a period of approximately eighteen years, demonstrates that the characteristics of the variety are firmly fixed.

The outstanding characteristic of my new variety is that it responds perfectly to date setting from either a cut or a pinch. A further unusual characteristic of this variety is the clinging quality of the petals, which rarely drop.

This new variety is similar to its parent in growth with the advantage of having more breaks and is a much freer bloomer. The flower differs from the parent in that the petals are predominantly red with variegated white striping, some extending from the base of the petal to the tip, some in a dot and dash effect varying in width, and on some petals on the perimeter or edge in the form of white blotches.

A further characteristic of this variety is its resistance to mildew. During ten years of experimentation with this plant at my greenhouse, I observed that it was the last variety to get mildew or yellow leaves while growing among other well known tea roses, some of which are patented.

THE PLANT

Growth: Makes long straight cane from a cut or pinch. Responds perfectly to date setting.

Blooming habit: Very free-blooming.

Disease resistance: Very healthy and resistant to mildew.

Stem: Strong and sturdy. Smooth, except on the lower part where there are a few small thorns, reddish in color. Eyes are far apart, making this an excellent cut flower variety.

Foliage:

*Quantity.*—Abundant.

*Type.*—From three to five leaflets.

*Color.*—Ivy Green Plate 1060 varying from 1060 to 1060/3 (Wilson's Horticultural Colour Chart, vol. II), underside of leaf Ivy Green 1060/3.

*Texture.*—Leathery.

*Leaf stems.*—Extra long.

*Shape.*—Long oval with rounded base.

*Size.*—Leaves are extra large.

THE FLOWER

Bud:

*Color.*—Ruby Red Plate 827 (Wilson's Horticultural Colour Chart, vol. II).

*Size.*—Approximately ½ x 1½—larger than its parent.

*Form.*—Urn-shaped.

*Peduncle.*—Very strong, holding flowers upright—no weak necks. No spines. Same color as stems.

*Calyx.*—Narrow and branched.

Flower:

*Form.*—High-centered and opens in spiral pattern. Petals open flat and hold their rose form until petals drop, never rolling back when open.

*Color.*—True color from bud stage to open rose with no fading. Ruby Red Plate 827 varying from 827 to 827/3 (Wilson's Horticultural Color Chart, vol. II) with variegated white striping from base to tip of some petals, and on others in a dot and dash effect with white blotches on the perimeter of the petals. Much brighter and outstanding when open.

*Size.*—Diameter 2¼" to 4"—about 2" in depth.

*Fragrance.*—Heavy.

*Petalage.*—35 to 52.

*Longevity.*—Very long since petals rarely drop.

Petals:

*Texture.*—Heavy and firm yet soft.

*Shape.*—Outer petals almost round. Center petals smaller than outer petals. Petals appear never to roll back, but open flat making large full rose.

*Size.*—1½" to 2"—center petals smaller.

Reproductive organs: Pistils and stamens rarely visible as flower holds its rose form. Three pistils to each flower, very light in color and short.

The color of this rose, together with its keeping qualities, response to date setting, and resistance to disease combine to make an outstanding commercial product.

Having thus disclosed the invention, I claim:

A new and distinct variety of rose plant, substantially as shown and described, characterized as to novelty by the outstanding striped markings, by its lasting qualities due to clinging of petals, by its habit of free blooming due to more breaks, by its perfect response to date setting, and by its resistance to mildew.

No references cited.